United States Patent [19]

Bell et al.

[11] Patent Number: 4,671,770
[45] Date of Patent: Jun. 9, 1987

[54] HIGH STRENGTH PORCELAIN DENTAL PROSTHETIC DEVICE

[75] Inventors: A. Milton Bell, Teaneck; Murray G. Gamberg, Manalapan; Ronald Kurzeja, Bridgewater, all of N.J.

[73] Assignee: Denpac Corp., Hackensack, N.J.

[21] Appl. No.: 674,966

[22] Filed: Nov. 26, 1984

Related U.S. Application Data

[63] Continuation-in-part of Ser. No. 596,314, Apr. 3, 1984, abandoned.

[51] Int. Cl.$^4$ ............................................. A61C 5/10
[52] U.S. Cl. ................................. 433/223; 433/222.1; 106/35; 264/19
[58] Field of Search ............... 433/223, 222, 218, 202, 433/203, 208; 106/35; 264/16, 19, 20

[56] References Cited

U.S. PATENT DOCUMENTS

| | | | |
|---|---|---|---|
| 3,464,837 | 9/1969 | McLean et al. | 106/35 |
| 3,541,688 | 11/1970 | McLean et al. | 433/208 |
| 3,761,728 | 9/1973 | Kochavi | 433/218 |
| 3,934,348 | 1/1976 | Janjie | 433/222 |
| 4,104,798 | 8/1978 | Takahashi et al. | 433/222 |
| 4,265,669 | 5/1981 | Starling et al. | 106/35 |
| 4,386,962 | 6/1983 | Walker | 433/222 |
| 4,431,451 | 2/1984 | Mabie et al. | 433/202 |

Primary Examiner—John J. Wilson
Attorney, Agent, or Firm—Lackenbach Siegel Marzullo & Aronson

[57] ABSTRACT

A high strength porcelain dental prosthetic device, such as an infrastructure, inlay or onlay is formed directly from a dental porcelain fired at elevated temperatures of about 1000° F. and above, under a pressure of about 10 to 1000 microns of Hg. A special furnace is devised which will achieve this pressure range in a rapid efficient manner. The resultant porcelain dental infrastructure has a high density, and the strength approaching that found in commercial cast ceramic restorations.

3 Claims, 2 Drawing Figures

HIGH STRENGTH PORCELAIN DENTAL PROSTHETIC DEVICE

RELATED PRIOR U.S. APPLICATIONS

This application is a continuation-in-part application of Ser. No. 596,314, filed Apr. 3, 1984, now abandoned.

FIELD OF THE INVENTION

This invention relates to dental reconstructive elements, with particular reference to fixed and removable dental prostheses. Specifically this invention relates to crowns and bridges, as well as inlays and onlays.

BACKGROUND AND DISCUSSION OF THE PRIOR ART

The conventional state of the art for the construction of crowns and bridges for dentistry is largely dependent upon the lost wax technique, which requires the casting of molten metal into an investment material employed to preserve the original form of a wax pattern.

The wax pattern is formed and designed to precisely fit either a die or model which is a replica of the tooth part prepared by the dentist to receive the crown or bridge to be fabricated. The wax pattern is duplicated in an alloy as either a full cast crown, a veneer crown, or a thimble-like coping, pontic, inlay or onlay, to which porcelain may be baked and bonded to form the finished element.

A summary of the state of the art is as follows and as further discussed in the article, "The Ceramic-Metal Restoration", *Quintessence of Dental Technology*, Oct. 1983, pp. 545-8, A. Milton Bell, D.D.S.

Various ceramic, metallic and ceramo-metal materials have been employed in attempts to improve crowns and bridges. Such materials are disclosed in U.S. Pat. No. 4,243,412, granted Jan. 6, 1981 to Jandon; U.S. Pat. No. 4,249,943 granted Feb. 10, 1981 to Mohammed, et al: U.S. Pat. No. 4,265,669, granted May 5, 1981 to Starling et al: U.S Pat. No. 2,206,502, granted July 2, 1940 to Heiligman; U.S. Pat. No. 3,649,732, granted Mar. 14, 1972 to Brigham et al; U.S. Pat. No. 4,321,042 granted Mar. 23, 1982 to Scheicher; U.S. Pat. No. 2,106,809 granted Feb. 1, 1938 to Prange, et al; U.S Pat. No. 3,450,545, granted June 17, 1969 to Ballard et al and U.S. Pat. No. 3,786,565 granted Jan. 22, 1974 to Jarrault. In general;

(1) The dentist prepares a tooth or teeth to be restored by one or more forms of fixed prosthodontic appliances dependent upon the nature of the restoration designed for the particular application (i.e. an inlay, onlay, crown, bridge, splint or fixed partial denture).

(2) The dentist must then impression the prepared tooth or teeth in an accurate manner in order to permit the accurate duplication of the patient's teeth to be restored by crowns or bridges. With this model or replica the dentist supplies an accurate duplication of the patient's opposing arch and a bite registration in what is known as centric relation. Thus a highly accurate duplication of the prepared teeth and the maxillo-mandibular relationship is prepared in model form on which the prosthesis is to be fabricated. Even in the restoration of a single crown, the dentist must provide the technician with an accurate duplication of the adjacent teeth as well as the opposing teeth in order to permit the building of contact points and occluding contact points in rest position of the jaws as well as in masticatory movements.

(3) Since the final restoration of a crown or bridge must harmonize with the patients' dentition in appearance as well as function, the precise model permits the fabrication of a wax pattern to conform to a specific design for a dental element.

(4) The finished wax pattern is sprued and then removed from the die or model and connected to a sprue former using a precise system of waxes to insure complete cast of the metal in the casting process. Since the wax pattern is removed from the die or model to be invested, this is considered to be an indirect fabrication technique. It is important to note this because discrepancies may be introduced in an indirect technique due to distortion of the wax pattern in the removal from the die. The wax may distort in the investing process, and the wax and investment materials undergo contraction and expansion changes due to temperature changes during burn-out and casting and solidification of the molten metal during the cooling cycle.

(5) The sprued wax pattern is then invested in a gypsum type of material such as cristobalite or a phosphate-bonded high heat material, depending upon the type of metal being cast.

(6) The invested wax pattern when set is placed into a burnout oven for a period of one and a half hours or more, depending upon the technique and metal being cast, and the manufacturers instructions of the particular investment used. Temperatures of the burn-out oven may range from 900 F. to 1600 F., and may involve one or more heat stages to insure maximum expansion of the investment to compensate for initial contraction during the setting of the investment. This expansion during the heating cycle varies and may be a cause for an improper fit of the final restoration, if not properly closely controlled. The burn-out procedure not only expands the investment in preparation for the casting of the molten metal, but is essential for the elimination of the wax thus leaving a void in the investment material or a mold of the eliminated wax pattern.

(7) It is customary to use a casting ring to contain the investment material around the wax pattern. Spacers are used to permit the expansion of the investment in the heating stage. This is an imprecise technique and can cause improper fit of the final casting. Some investment materials use a plastic or paper ring for the purpose of forming and containing the investment material for the casting procedure. The plastic or paper is burned off during the burn-out stage or removed after the investment has set. This allows for maximum expansion of the investment during the heating stage. The actual casting is done by placing the investment which was formed by some kind of device, or in a steel ring, into some type of casting apparatus after the burn-out stage. This permits the melting of the desired metal at the required temperature, and the molten metal is then forced into the mold in the hot investment either by centrifugal force, pressure or vacuum. Conventional dental ovens provide for maximum vacuum pressures of 26-29 in. Hg, ie. about 60,000 microns Hg. These ovens were typically used as porcelain firing furnaces. There are various types of equipment for these different methods of making a casting. Once the cast has been completed, the metal and investment material must be allowed to cool.

(8) The casting can be recovered from the investment material by breaking out the casting from the investment. The casting is then cleaned of any remnants of the investment material.

(9) The sprues must then be cust off the crown, bridge or pontic and smoothed down. The casting must then be fitted back upon the original die. If the technique employed by the technician utilizes a gypsum die it may be difficult to seat the casting on the model without scraping or chipping the die. The ultimate fit on the tooth is therefore complicated for the dentist.

Miscasts and incomplete castings which fail to reproduce fine margins or parts of the original wax pattern, or poor fit of the casting due to shrinkage and expansion factors of the wax and investment materials is not uncommon. This may require repeating the entire procedure if the casting cannot be properly seated on the die or prepared tooth of the patient.

While dental bridges can either be cast in one piece or assembled from individual units, a more accurate fit is assured by assembly of the units of the bridge or splint from an index impression taken of the units seated in the mouth, which may insure complete placement of the castings upon the individual prepared teeth. This technique has been widely employed for many years, utilizing the precious alloys which are relatively simple to solder. The non-precious alloys employed today are more difficult to solder or braze due to their formation of high oxide layers on their surfaces when subjected to high temperatures during this process. This has led the dentist to prescribe having their technicians cast multiple unit bridges and splints in one piece to eliminate the necessity for soldering. There is some question as to the accuracy of fit of such long span prostheses being cast as one piece.

In Starling et al, U.S. Pat. No. 4,265,669, there is disclosed an attempt for preparing a high strength ceramic crown material.

Another prior art attempt at achieving a high strength ceramic is the "Dicor" process of Dentsply International, Inc., York, Pa. 17405. ("Dicor" is a trademark of Dentsply International, Inc., a subdivision of Coors).

While such prior art attempts at high strength ceramic crown materials provided commercially acceptable strengths, they involved multi-step, laborious, time-consuming processes.

The long, labor intesive prior art metal coping as process well as ceramic crown processes were costly as well as time consuming, and sometimes provided a questionable or inaccurate fit.

Now there is provided by the present invention a direct method for the preparation of high strength all porcelain crown, inlays and onlays which avoid many of the aforesaid prior art problems.

It is a principal object of the present invention to provide a direct method and resultant all porcelain highly aesthetic, strong prosthetic product.

It is another principal object of the present invention to provide a method and dental prosthetic product as aforesaid in which tooth reduction is minimized, in addition to better aesthetics there is high biocompatibility, elimination of thermal shock; radioluscence to X-ray; and ease of use and cleaning by the user.

These objects, as well as other objects, will become apparent from the reading of the following description, the adjoined claims, and the accompanying drawings, in which:

SUMMARY OF THE INVENTION

Figure 1:
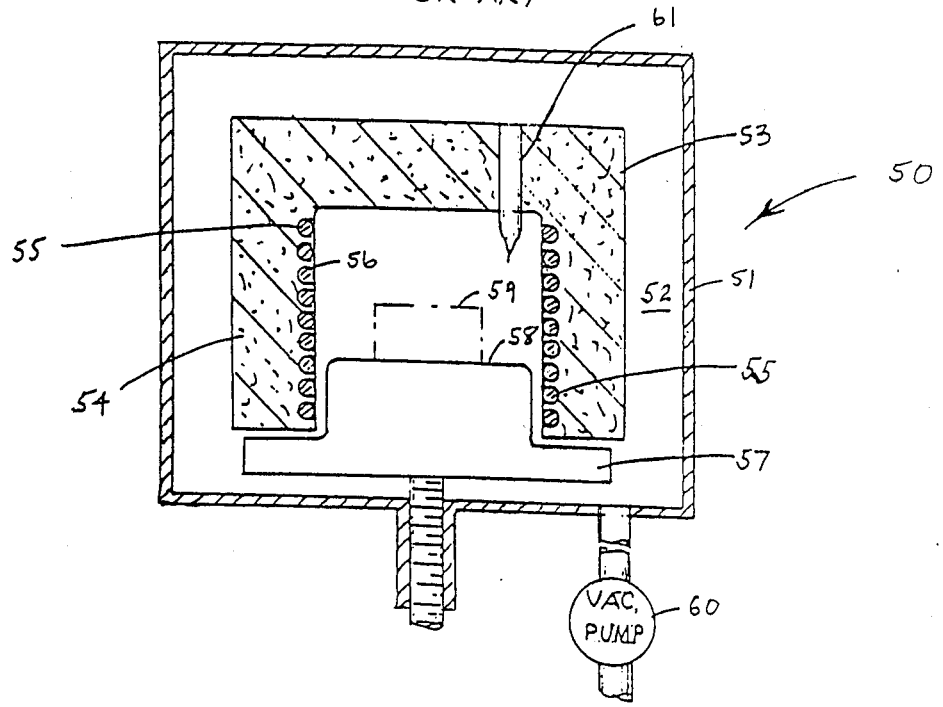
FIG. 1 is a schematic partial sectional view of a prior art dental furnace.

A direct method for the formation of dental prosthetic infrastructure component or inlay which eliminates the metal component, such as a dental alloy coping, or gold inlay, or silver amalgam filling and wherein the component is formed of a dental porcelain under a vacuum of 10-1000 microns Hg. on a refractory die. Infrastructure porcelain or inlay is fired at about 1800°-1900° F. under high pressure to form a replica of the tooth surface, and for crowns, the porcelain is directly bonded to the infrastructure porcelain. The infrastructure porcelain has commercially acceptable high levels of strength in the order of 15,000 to 20,000 psi in flexural modulus. A novel furnace is provided to provide reliable vacuum firing of the infrastructure porcelain, or all porcelain inlay.

DESCRIPTION OF THE PREFERRED EMBODIMENTS

In one broad sense the present invention may be said to be a vacuum firing process for forming a dental porcelain infrastructure to which a relatively thin layer of porcelain may be directly bonded, so as to form a restorative element or appliance, such as a crown or bridge. The accuracy of fit enhanced by the novel controlled expansion/contraction refractory die material, plus the added strength of the porcelain due to the novel sintering technique of the special furnace, permits the fabrication of highly aesthetic compatible inlays or onlays. The porcelain in these techniques is fired at about 1879° F. under pressures of about 10-1000 microns of Hg., and preferably 10-100 microns of Hg.

In another broad sense, the invention is a method for making the dental reconstructive or restorative element, which includes the following steps:

(a) forming an impression mold of a tooth surface so as to form a cavity replicating the prepared tooth surface;
(b) mixing a pourable refractory material;
(c) filling the cavity with said refractory material;
(d) separating the die from the mold;
(e) firing the refractory material to form a solid die, having a replicate of the tooth surface;
(f) covering the replicate surface with slurry of porcelain;
(g) drawing vacuum in the oven to about 10 to 1000 microns Hg;
(h) firing the porcelain in the furnace to form the infrastructure or inlay component of the prosthetic element; and
(i) in crowns, bonding a porcelain material to the infrastructure porcelain.

It is an important aspect of the present invention (in the construction of inlays, bridges and crowns) that whereas the prior art required extensive tooth reduction so as to allow for a metal coping of about 0.3 mm, an opaque porcelain layer of 0.3-0.4 mm followed by a gingival porcelain outer layer of approximately ½-1 mm., the present invention only requires an opaque porcelain infrastructure of about ½ mm with a gingival porcelain outer layer of about ½ mm, thereby by reducing tooth reduction by from 0.3 mm to 1 mm or more.

Other improvements provided by the present invention include (A) less chance of exposing the nerve inasmuch as tooth reduction is reduced (B) better fit, and (C) better aesthetics.

The finished restorative structure of the present invention will exhibit a flexural modulus of 15,000 to 20,000 psi. This finished structure will have a porosity of less than 1.50% and preferably less than 1.00%.

Suitable porcelains useful for the infrastructure of the present invention include the following:

TABLE A

| Compound | Weight % |
|---|---|
| $SiO_2$ | 47-54 |
| $Al_2O_3$ | 9-14 |
| $K_2O$ | 8-10 |
| $Na_2O$ | 4-6 |
| $Li_2O$ | 0-2 |
| $B_2O_3$ | 0-3 |
| CaO | 0-2 |
| MgO | 0-0.5 |
| $SnO_2$ | 18-20 |

It is also understood that $TiO_2$ and $ZrO_2$ may be useful opacifying components in addition to or in lieu of the $SnO_2$. $Al_2O_3$ may be substituted for the $SnO_2$ in equivalent amounts of 18-20%.

In practicing the invention a pourable refractory die material is used to replicate the tooth or teeth preparations as impressioned by the dentist, in order to construct the die or working model.

(1) The die material being a refractory material is dimensionally stable at the temperatures of at which the porcelain is fired.

(2) The new refractory material is formed from a powder-liquid formulation and is mixed in a recommended ratio of powder to liquid so as to produce a pourable, easy flowing material. This reduces the possibility of bubbles. The refractory mass is easy to handle and sets in a relatively short time span permitting retrieval from the impression, with ease of initial trimming prior to firing.

(3) Depending upon the particular type of prosthestic component, the refractory die material may be designed to expand or contract within controlled limits of up to 3%, and preferably 1-2% linear thermal expansion, only upon the initial firing of the die (model) to compensate and allow for accurate fit.

(4) The refractory material is compatible with all types of opaque dental porcelains and should accept a separating medium or release agent which will prevent the porcelain from adhering to the die or model material.

The refractory die material is essentially a ceramic or mineral system. The refractory die material would preferably be a combination of a silicate mineral and colloid of silica. The silicate mineral may be cristobalite.

A preferred commercially available refractory die is the porcelain Die Material manufactured by Whip Mix Corp., Louisville, Ky 40217. This powder is mixed with porcelain die material liquid, colloidal silica, to make the material a flowable suspension. The flowable suspension should be in the range of 20 ml./100 gm. to 25 ml./100 gm. (The liquid is believed responsible for both the green and fired strength of the die). The suspension permits approximately five minutes working time before it undergoes an initial set. This working time may be altered if desirable. The material continues to harden nd should be allowed to bench-set for thirty to sixty minutes at which time it can be retrieved from the impression mold.

After pouring, a special alumina dowel is inserted in the poured refractory molds. This special dowel can withstand the high sintering temperatures and multiple firings without interfering with the porcelain fabrication procedures. The special dowel may be machined from a number of inert compatible materials, but the preferred material is a high alumina formulation.

When pouring the refractory material into the dental impression, the alumina dowel is placed and fixed into position. (After the initial set the die may be removed from the impression and trimmed.) The die is then reseated into the impression in such a fashion so that a master model can be constructed which would permit the die to be removed and reseated by use of the dowel which acts as an accurate seating key. The die and model are then removed from the impression and the die is separated from the model and fired.

It is also within the contemplation of the invention to use a wetting and release/separating medium or agent on the refractory die material to enhance the removal of the fired porcelain, particularly so for the fitting or try-in phase by the dentist. Useful separating agents include the ceramic cast separating agent manufactured by Aremco, Briarcliff Manor, NY. and the fluorocarbon release agent MS-145 manufactured by Miller-Stephenson Chemical Co. Inc., Los Angeles, Calif. The refractory die may also be used as a sagger tray in holding the crown in the furnace during the porcelain firing cycle.

Referring to FIG. 1 there is a typical prior art dental oven 50. Oven 50 is formed with an outer housing 51 which in effect provides a vacuum chamber 52. A muffle 53 is disposed within the vacuum chamber 52. Muffle 53 is formed of a thick fibrous insulatory material 54 with heating elements 55 disposed at the inner circumferential surface 56. A reciprocating base 57 having a specimen platform 58 for mounting specimen 59, reciprocates in relationship to muffle 53 so as to enclose the specimen 59 for direct heating by elements 55. A vacuum pump 60 is operably connected to the outer housing 51. Pump 60 and housing 51 are designed to achieve pressures of about 60,000 microns of Hg. The use is primarily for porcelain bonding operations. A thermocouple 61 completes the assembly.

Figure 2:
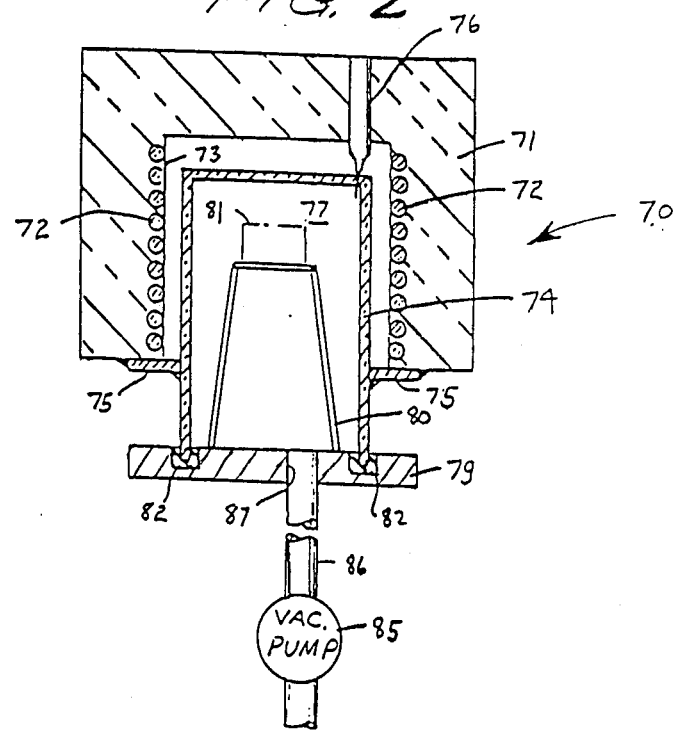
FIG. 2 is a schematic partial sectional view of the dental furnace used in the present invention.

Referring to FIG. 2 there is shown the oven used in the present invention 70. Oven 70 is formed of an outer insulated member 71 having heating elements 72 disposed on the inner cylindrical surface 73. A non-fibrous alumina or mullite muffle or inverted cup 74, or ¼ to ⅜ inch thickness, is disposed on the inside of heating elements 72. Cylindrical inverted cup 74 is fixedly connected to member 71 by well known structural elements 75. Thermocouple 76 is mounted through member 71 and cup 74 for measuring the temperature within chamber 77. The assembly of 71 and 74 is mounted to well known reciprocating means (not shown) for the vertical reciprocation of this assembly for purposes hereinafter immediately appearing. A base 79 is provided with a mounting platform 80 disposed thereon for supporting a dental prosthetic preform 81. Annular seal 82 is provided on base 79 for providing a vacuum seal between cup 74 and base 79 when the assembly is vertically lowered to mate with the base. Vacuum pump 85 is mounted immediately adjacent the fixed base 79 and interconnected to chamber 77 by conduits 86 and 87.

Pump 85 is capable of drawing a maximum of 0.1 micron Hg.

In this manner of construction there is a rapid accurate high vacuum maintained between 10 to 1000 microns Hg, and preferably 10 to 100 microns Hg. The close fixed mounting of the vacuum pump to the chamber permits a fast accurate high level of vacuum to be maintained. In addition the dense alumina muffle 74 permits rapid high vacuum without breakdown of a fibrous structure. The dense alumina muffle also permits rapid indirect heating of the preform within the chamber.

The following Example is illustrative of the invention:

THEORETICAL EXAMPLE

An impression of the tooth is taken by the well known technique. A final mixture of 21 ml. of Whip Mix Porcelain Die Material Liquid and 100 grams of the Whip Mix Porcelain Die Material is mixed in a container. The mixture is then vibrated into the cavity and an alumina dowel is inserted into the mixture. The mixture is allowed to set at room temperature for about 30 to 60 minutes. the die is then removed, trimmed, placed back and set into the impression. A master model is then constructed. The die and model are then removed from the impression. The die is then separated from the model and placed into the furnace and fired.

Porcelain material as shown in Table A is provided. The powdered opaque porcelain is mixed with distilled water in a ratio of 1 part water: 5 parts porcelain to the consistency of a light paste, and then brush applied in an up to 0.5 mm coating on the die, and air dried. The porcelain-die is vibrated and the excess water is then blotted and dried off. The porcelain preform is then pre-dried; in front of an open furnace at 1200° F. The coated die is then fired in a furnace to 1800° F., at a rate of 100° F./min., to form the solid porcelain infrastructure component. A layer of porcelain may then be bonded to the infrastructure porcelain by conventional porcelain bonding techniques.

Thus there has been shown a novel direct approach to obtain a dental crown or bridge through the use of the refractory die and opaque porcelain infrastructure.

The novel method and furnace now permit direct rapid formation of a permanent prosthetic while the patient waits. This method can be accomplished in no more than about 1-1½ hours.

While we have described herein certain embodiments of our invention, we intend to cover as well any change or modification therein that may be made without departure from its spirit and scope.

What is claimed is:

1. A dental crown comprising a porcelain infrastructure and a gingival porcelain cover bonded directly to the porcelain infrastructure, (and) wherein the thickness of the infrastructure porcelain is not greater than about 0.5 mm and the thickness of the gingival porcelain cover is not greater than 0.5 mm, the infrastructure porcelain has a flexural modulus of about 15,000 to about 20,000 psi, a porosity less than about 1.5%, and an alumina content from about 9% to about 34% by weight.

2. The dental crown of claim 1, wherein the infrastructure consists essentially of a dental porcelain.

3. A method for forming a dental restorative infrastructure element comprising:
    (a) forming an impression of a surface;
    (b) mixing a refractory material;
    (c) filling the impression with said refractory material to form a die preform;
    (d) separating the die preform from the impression;
    (e) firing the refractory material to form a solid die having a replicate of the surface;
    (f) covering the surface replicate with a slurry of dental porcelain comprising from about 9% to about 34% by weight of alumina;
    (g) drawing down pressure to 10 to 1000 microns Hg;
    (h) firing the porcelain so as to form a porcelain dental infracture restorative element having a flexural modulus of 15,000 to 20,000 psi and a porosity less than about 1.5%, said element being permanent and being formed in no more than about 1 to 1½ hours.

* * * * *